(12) United States Patent
Suzuki et al.

(10) Patent No.: US 11,530,992 B2
(45) Date of Patent: Dec. 20, 2022

(54) GAS DETECTION ELEMENT

(71) Applicant: Nitto Denko Corporation, Osaka (JP)

(72) Inventors: Namiko Suzuki, Osaka (JP); Hiroyuki Higuchi, Osaka (JP); Koichi Nakamura, Osaka (JP); Masaya Nishigawara, Osaka (JP); Nahid Mohajeri, Merritt Island, FL (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 16/637,451

(22) PCT Filed: Aug. 2, 2018

(86) PCT No.: PCT/JP2018/029036
§ 371 (c)(1),
(2) Date: Feb. 7, 2020

(87) PCT Pub. No.: WO2019/031383
PCT Pub. Date: Feb. 14, 2019

(65) Prior Publication Data
US 2020/0249174 A1    Aug. 6, 2020

(30) Foreign Application Priority Data

Aug. 8, 2017  (JP) .............................. JP2017-153596
Aug. 1, 2018  (JP) .............................. JP2018-145006

(51) Int. Cl.
*G01N 21/78* (2006.01)
*G01N 33/00* (2006.01)
*G01N 31/22* (2006.01)

(52) U.S. Cl.
CPC ......... *G01N 21/783* (2013.01); *G01N 31/223* (2013.01); *G01N 33/005* (2013.01)

(58) Field of Classification Search
CPC ........ G01N 21/75; G01N 21/77; G01N 21/78; G01N 21/783; G01N 31/22; G01N 31/223; G01N 31/224; G01N 33/005
See application file for complete search history.

(56) References Cited

U.S. PATENT DOCUMENTS 4,256,694 A     3/1981 McAllister et al.
4,587,102 A *   5/1986 Nagatomo ........... G01N 33/525
                                                422/421
(Continued)

FOREIGN PATENT DOCUMENTS

CN    106093295    11/2016
CN    110291234     9/2019
(Continued)

OTHER PUBLICATIONS

International Search Report dated Oct. 23, 2018 with respect to PCT/JP2018/029036.
(Continued)

*Primary Examiner* — Benjamin R Whatley
*Assistant Examiner* — Austin Q Le
(74) *Attorney, Agent, or Firm* — IPUSA, PLLC

(57) ABSTRACT

A gas detection element for detection of a measurement target gas is provided. The gas detection element includes a gas detection layer including a chemochromic pigment; and a spacer. The spacer is permeable to the measurement target gas, is disposed on a first surface of the gas detection layer, and has an area smaller than an area of the gas detection layer.

17 Claims, 9 Drawing Sheets

(56) References Cited

U.S. PATENT DOCUMENTS

| | | | |
|---|---|---|---|
| 5,310,525 A | 5/1994 | Churchouse et al. | |
| 5,552,276 A * | 9/1996 | Mochida | G01N 33/543 435/6.19 |
| 5,849,073 A * | 12/1998 | Sakamoto | C09D 7/68 106/437 |
| 5,989,840 A | 11/1999 | D'Angelo et al. | |
| 8,048,384 B1 | 11/2011 | Bokerman et al. | |
| 8,293,178 B2 | 10/2012 | Roberson et al. | |
| 8,591,818 B2 | 11/2013 | Bokerman et al. | |
| 8,652,993 B2 | 2/2014 | Mohajeri | |
| 8,703,642 B2 | 4/2014 | Mohajeri | |
| 8,920,730 B2 | 12/2014 | Roberson et al. | |
| 8,945,473 B2 | 2/2015 | Roberson et al. | |
| 2005/0089260 A1 | 4/2005 | Mechery et al. | |
| 2005/0186117 A1 | 8/2005 | Uchiyama et al. | |
| 2007/0089989 A1 | 4/2007 | Hoagland et al. | |
| 2007/0251822 A1* | 11/2007 | Hoagland | G01N 31/22 204/424 |
| 2010/0089123 A1* | 4/2010 | Fukui | G01N 33/005 73/31.06 |
| 2012/0272728 A1 | 11/2012 | Fukui et al. | |
| 2014/0007887 A1* | 1/2014 | Joly | B01D 46/0086 128/863 |
| 2014/0154808 A1* | 6/2014 | Patel | A61L 2/07 436/1 |
| 2016/0011157 A1* | 1/2016 | Smyth | G01N 31/229 422/426 |
| 2020/0003697 A1 | 1/2020 | Nakamura et al. | |
| 2020/0124538 A1 | 4/2020 | Nakamura et al. | |
| 2020/0124579 A1 | 4/2020 | Nakamura et al. | |

FOREIGN PATENT DOCUMENTS

| | | |
|---|---|---|
| EP | 3012629 | 4/2016 |
| JP | H08-253742 | 10/1996 |
| JP | 2005-233740 | 9/2005 |
| JP | 2005-345338 | 12/2005 |
| JP | 2008-082980 | 4/2008 |
| JP | 2011-013079 | 1/2011 |
| JP | 2011-013080 | 1/2011 |
| JP | 2016-161507 | 9/2016 |
| WO | 2018/152430 | 8/2018 |
| WO | 2018/152431 | 8/2018 |

OTHER PUBLICATIONS

Partial supplementary European search report dated Apr. 8, 2021 issued with respect to the corresponding European patent application No. 18844276.8.

Extended European Search Report dated Jul. 26, 2021 with respect to the corresponding European Patent Application No. 18844276.8.

Office Action dated Jan. 5, 2022 issued with respect to the corresponding Chinese patent application No. 201880050841.X.

* cited by examiner

GAS DETECTION ELEMENT

TECHNICAL FIELD

The present application relates to a gas detection element.

BACKGROUND ART

Hydrogen gas is used in various applications, including energy generation means such as batteries, energy storage means, and energy transfer means.

Hydrogen gas is a colorless, odorless, and flammable gas having a wide flammability limit in the air. Therefore, it is required to properly detect hydrogen gas leakage for safety purposes in any environment and/or apparatus in which hydrogen gas is handled.

In the past, methods using soapy water and a hydrogen sensor have been employed to detect hydrogen gas leakage.

Of these methods, the method using soap water requires complicated measurement preparation, and also has difficulty in determining the presence of gas bubbles if the amount of hydrogen gas leakage is small. Therefore, the detection accuracy is poor in the method using soap water. Further, the method using the hydrogen sensor is susceptible to the flow of air in a measurement environment, thus resulting in a decrease in reliability. In addition, the method using the hydrogen sensor has difficulty in identifying the accurate location of leakage.

In light of the above, in order to more accurately and simply detect hydrogen gas leakage, the use of a hydrogen detection tape has been proposed.

The hydrogen detection tape includes a chemochromic pigment that changes in color by contacting hydrogen gas. Accordingly, the presence of the hydrogen gas can be detected by the change in color of the chemochromic pigment (Patent Documents 1 to 7, for example).

RELATED-ART DOCUMENTS

Patent Documents

Patent Document 1: U.S. Pat. No. 8,048,384
Patent Document 2: U.S. Pat. No. 8,591,818
Patent Document 3: U.S. Pat. No. 8,652,993
Patent Document 4: U.S. Pat. No. 8,703,642
Patent Document 5: U.S. Pat. No. 8,293,178
Patent Document 6: U.S. Pat. No. 8,920,730
Patent Document 7: U.S. Pat. No. 8,945,473

SUMMARY OF THE INVENTION

Problem to be Solved by the Invention

In use, the hydrogen detection tape is attached to an inspection member such as a pipe where hydrogen gas leakage may occur. If hydrogen gas leaks from the inspection member, a region of the hydrogen detection tape, corresponding to the location of leakage, changes in color. Accordingly, the hydrogen gas leakage can be detected.

In such a case, if the location where the hydrogen gas has leaked is very small, the region of the hydrogen detection tape where the color changes becomes also very small.

If the region where the color changes is very small, the visibility of the color change decreases, thus making it difficult for an inspector to properly determine leakage of hydrogen gas.

For example, in hydrogen stations, which are expected to be widely used in the future, leakage ports are installed to detect leakage of hydrogen gas. However, the opening of such a leakage port is assumed to be as small as approximately 1 mm to 3 mm in diameter. If a hydrogen detection tape is attached to such a very small leakage port in a hydrogen station, a problem may arise with respect to color change visibility as described above.

The present invention is made in light of the above problem, and aims at providing a gas detection element that significantly enhances the visibility of measurement target gas leakage.

Means to Solve the Problem

The present invention provides a gas detection element for detection of a measurement target gas. The gas detection element includes a gas detection layer including a chemochromic pigment, the gas detection layer having a first surface; and a spacer. The spacer is permeable to the measurement target gas, is disposed on the first surface of the gas detection layer, and has an area smaller than an area of the gas detection layer.

Further, the present invention provides a gas detection element for detection of a measurement target gas. The gas detection element includes a gas detection layer including a chemochromic pigment, the gas detection layer having a first surface. The first surface of the gas detection layer has a space to be filled with the measurement target gas, and the space has an area smaller than an area of the gas detection layer.

Effects of the Invention

It is possible to provide a gas detection element that significantly enhances the visibility of measurement target gas leakage.

MODE FOR CARRYING OUT THE INVENTION

In the following, embodiments of the present invention will be described with reference to the drawings.

In the following description, as an application example of an embodiment of the present invention, a gas detection element for detection of hydrogen gas will be described. However, it should be noted that the gas detection element according to the present invention may also be used to detect any reducing gas other than hydrogen gas.

As used herein, the "reducing gas" refers to a gas containing at least one of hydrogen, hydrogen sulfide, carbon monoxide, methane, formaldehyde, acetylene, sulfur dioxide, and nitrous oxide.

(Gas Detection Element According to Embodiment of Present Invention)

Figure 1:
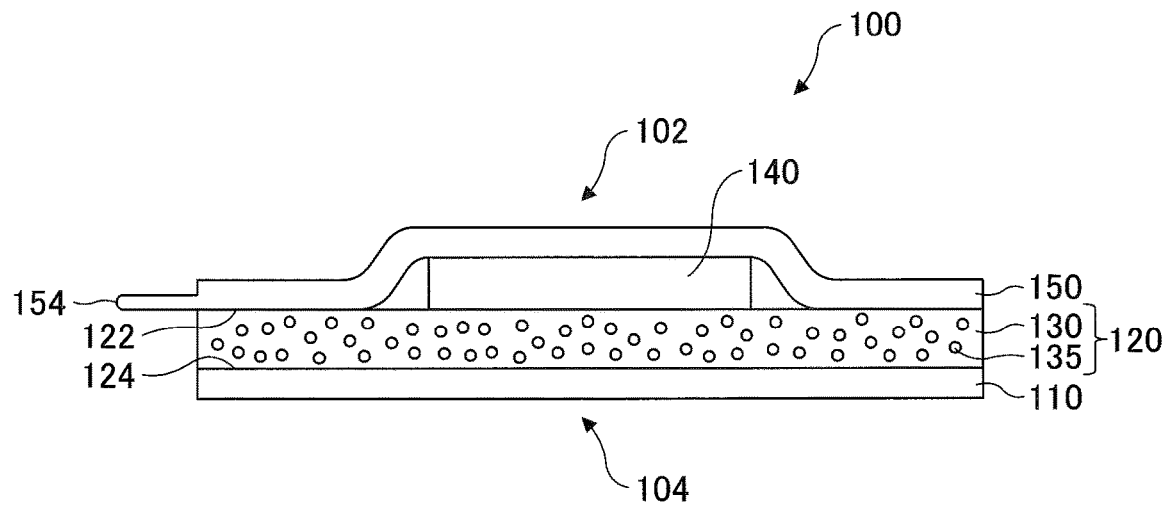
FIG. 1 is a cross-sectional view schematically illustrating a configuration example of a gas detection element according to an embodiment of the present invention.

FIG. 1 schematically illustrates a configuration example of a gas detection element (hereinafter referred to as a "first gas detection element") according to an embodiment of the present invention.

As illustrated in FIG. 1, a first gas detection element 100 has a first side 102 and a second side 104.

Further, the first gas detection element 100 includes a backing 110, a gas detection layer 120, a spacer 140, and a release liner 150. The backing 110 constitutes the second side 104 of the first gas detection element 100. The release liner 150 constitutes the first side 102 of the first gas detection element 100. However, one or both of the backing 110 and the release liner 150 may be omitted.

The backing 110 serves to support the gas detection layer 120 and other elements disposed on and above the detection layer 120.

The gas detection layer 120 includes a first surface 122 and a second surface. The second surface 124 is a surface of the gas detection layer 120 on the side close to the backing 110, and the first surface 122 is a surface of the gas detection layer 120 on the side far from the backing 110. If the backing 110 is omitted, the second surface 124 of the gas detection layer 120 may serve as the second side 104 of the first gas detection element 100.

The gas detection layer 120 serves to detect hydrogen gas. More specifically, when the gas detection layer 120 contacts hydrogen gas, the color of the gas detection layer 120 changes. Accordingly, the gas detection layer 120 can detect the presence of the hydrogen gas.

Although not illustrated in FIG. 1, the first gas detection element 100 may further include an adhesion layer (an undercoat layer) between the backing 110 and the gas detection layer 120. The adhesion layer serves to enhance adhesion between the backing 110 and the gas detection layer 120. However, the adhesion layer may be omitted, if not necessary.

The gas detection layer 120 includes a resin matrix 130 and a chemochromic pigment 135 added to the resin matrix 130.

The chemochromic pigment 135 includes a material that changes in color by contacting hydrogen gas. For example, palladium oxide is known to change in color by contacting hydrogen gas. Therefore, the chemochromic pigment 135 may include palladium oxide.

The gas detection layer 120 has adhesiveness.

The spacer 140 is disposed on the first surface 122 of the gas detection layer 120. The spacer 140 is permeable to hydrogen gas. Therefore, when hydrogen gas enters the spacer 140, the hydrogen gas is relatively rapidly diffused throughout the spacer 140.

The spacer 140 is configured to have an area smaller than the area of the gas detection layer 120 when viewed from the second side 104. For example, when viewed from the second side 104, the periphery of the spacer 140 is surrounded by the gas detection layer 120.

As an example, the spacer 140 is assumed to have an approximately circular shape in top view. However, it is obvious that the shape of the spacer 140 is not limited to the approximately circular shape.

The release liner 150 serves to cover the gas detection layer 120 and other elements (such as the spacer 140) disposed on the first surface 122.

That is, if the first surface 122 is exposed, the handleability of the first gas detection element 100 may decrease because of the adhesiveness of the gas detection layer 120. By providing the release liner 150, it is possible to avoid the exposure of the first surface 122 of the gas detection layer 120, thus allowing the first gas detection element 100 to be readily handled.

However, as described above, in the present invention, the release liner 150 is not required to be provided, and may be omitted. If the release liner 150 is omitted, the first surface 122 of the gas detection layer 120 and the spacer 140 function as the first side 102 of the first gas detection element 100.

As illustrated in FIG. 1, the release liner 150 may have a protruding portion 154 at one or both ends.

In the example illustrated in FIG. 1, the protruding portion 154 is formed by decreasing the thickness of the release liner 150. However, the protruding portion 154 may be formed by extending the release liner 150 to the outside without changing the thickness of the release liner 150. Alternatively, the protruding portion 154 may be formed by processing the shape of the end of the release liner 150.

By providing the protruding portion 154, the release liner 150 is readily removed from the first gas detection element 100.

Alternatively, a cut line may be formed on the outer surface of the release liner 150, thereby allowing the release liner 150 to be readily removed.

Figure 2:
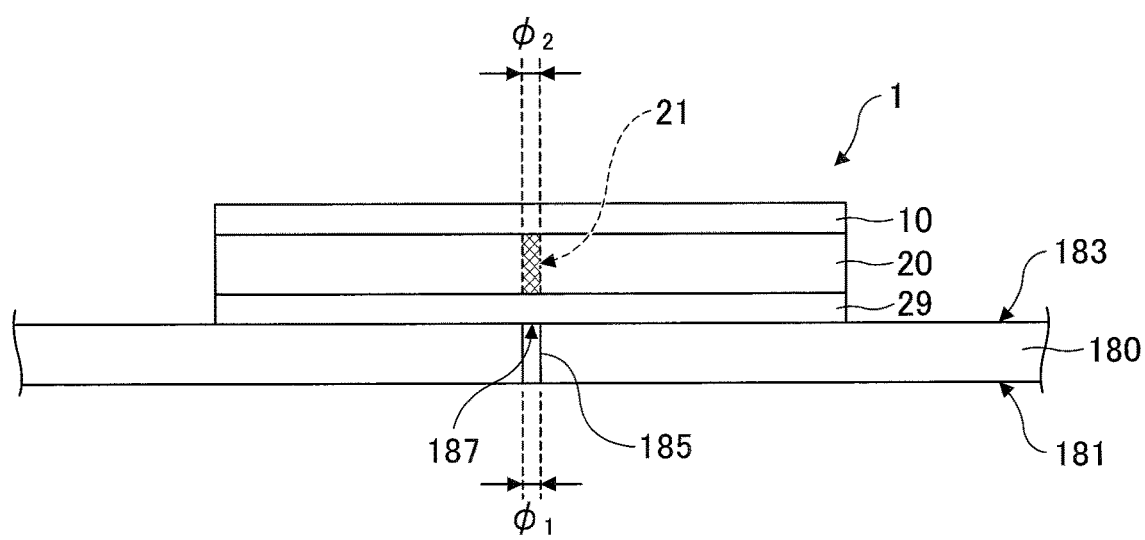
FIG. 2 is a cross-sectional view schematically illustrating an application example of a conventional hydrogen detection tape.

Referring now to FIG. 2, for better understanding of features and effects of the gas detection element according to the embodiment of the present invention, an application example of a conventional hydrogen detection tape will be described.

FIG. 2 schematically illustrates an example of a conventional hydrogen detection tape attached to an inspection member.

As illustrated in FIG. 2, a conventional hydrogen detection tape 1 includes a backing 10, a hydrogen gas detection layer 20, and an adhesive layer 29, which are stacked in this order.

An inspection member 180 is assumed to have a first surface 181 and a second surface 183. Further, it is assumed that a space is formed on the second surface 183 side of the inspection member 180, and a hole 185 is formed through the inspection member 180 from the first surface 181 to the second surface 183. The hole 185 leads to the space. An opening 187 of the hole 185 is formed on the second surface 183 of the inspection member 180, and the opening 187 has a diameter φ1.

As illustrated in FIG. 2, an example in which the conventional hydrogen detection tape 1 is attached to the inspection member 180 is assumed. In this state, if hydrogen gas leaks from the hole 185 of the inspection member 180, the color of a region of the hydrogen gas detection layer 20 facing the opening 187 of the hole 185 changes. Therefore, by observing a color change region 21, leakage of hydrogen gas can be detected from the backing 10 side.

Typically, the color change region 21 of the hydrogen gas detection layer 20 has the same diameter as the diameter φ1 of the opening 187 of the hole 185, or has a slightly larger diameter φ2.

However, in a hydrogen gas detection method using the above-described conventional hydrogen detection tape 1, if the diameter φ1 of the opening 187 of the hole 185 is small, the diameter φ2 of the color change region 21 of the hydrogen detection tape becomes also small. Therefore, with the opening 187 being very small, the inspector may be unable to properly detect leakage of hydrogen gas.

According to an embodiment of the present invention, the above-described problem can be significantly minimized or eliminated.

In the following, such an effect will be described in detail with reference to FIG. 3.

Figure 3:
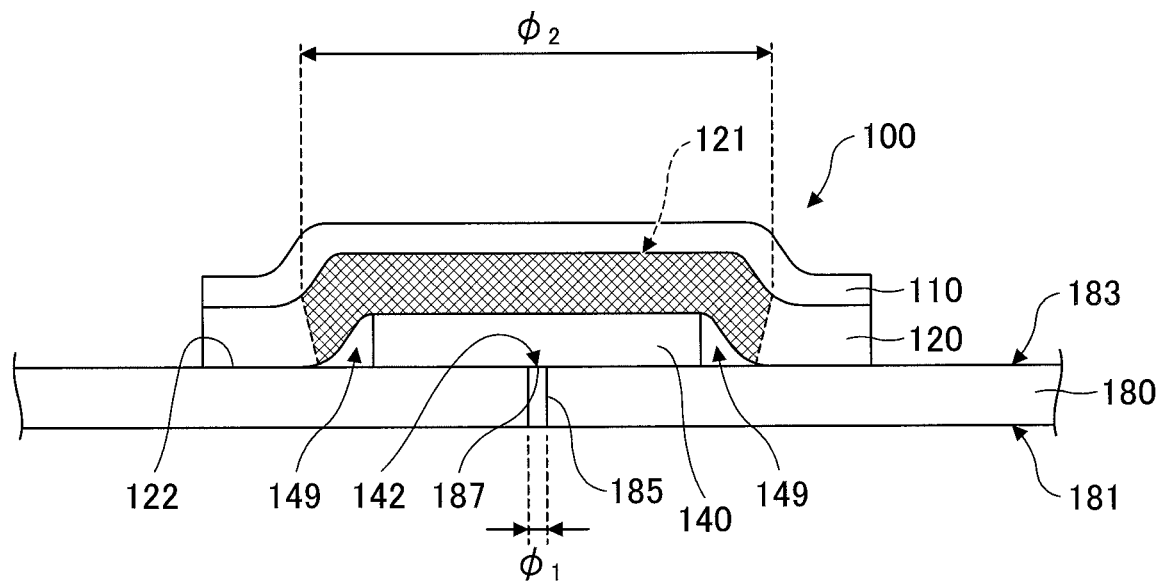
FIG. 3 is a cross-sectional view schematically illustrating an application example of the gas detection element according to the embodiment of the present invention.

FIG. 3 schematically illustrates an example in which the first gas detection element 100 having the configuration as illustrated in FIG. 1 is attached to the inspection member 180. For ease of illustration, the chemochromic pigment 135 included in the gas detection layer 120 is not depicted in FIG. 3.

When the first gas detection element 100 is actually used for the inspection member 180, the release liner 150 is first removed from the first gas detection element 100 having the configuration as illustrated in FIG. 1. At this time, the protruding portion 154 may be used to remove the release liner 150. By peeling the release liner 150 while holding the protruding portion 154, the release liner 150 can be readily separated from the other members of the first gas detection element 100.

Next, the first gas detection element 100 is attached to the inspection member 180. At this time, the first gas detection element 100 is attached in such a manner that the first surface 122 of the gas detection layer 120 and the spacer 140, exposed by the removal of the release liner 150, are brought into contact with the inspection member 180.

In this manner, the spacer 140 is positioned over the opening 187 of the inspection member 180 as illustrated in FIG. 3. A region of the spacer 140 facing the opening 187 is hereinafter referred to as a "contact region (142)".

Further, because the gas detection layer 120 has adhesiveness, the first gas detection element 100 is fixed onto the inspection member 180 by the adhesion of the gas detection layer 120. At this time, the periphery of the spacer 140 is surrounded by the gas detection layer 120, and thus, the position of the spacer 140 on the inspection member 180 is fixed.

Note that a gap 149 may be formed between the gas detection layer 120 and the spacer 140 along the periphery of the spacer 140 as illustrated in FIG. 3.

In this state, if hydrogen gas leaks from the hole 185 of the inspection member 180, the leaked hydrogen gas enters the first gas detection element 100 from the region facing the opening 187 of the first gas detection element 100, namely from the contact region 142.

As described above, the spacer 140 is permeable to hydrogen gas. Therefore, the hydrogen gas, which has entered the first gas detection element 100 from the contact region 142 of the spacer 140, is rapidly diffused into the spacer 140 upward and laterally. Then, the hydrogen gas spreads throughout the contact surface between the first surface 122 of the gas detection layer 120 and the spacer 140. Further, the presence of the spacer 140 allows the hydrogen gas to flow around the spacer 140. If the gap 149 is formed around the spacer 140, the gap 149 is filled with the hydrogen gas.

Accordingly, a wide area of the first surface 122 of the gas detection layer 120 contacts the hydrogen gas. In particular, as compared to the conventional hydrogen detection tape 1 described with reference to FIG. 2, a large color change region 121 can be obtained. For example, in the example illustrated in FIG. 3, the color change region 121 has a diameter φ2 that is sufficiently larger than the diameter φ1 of the opening 187 of the hole 185.

Further, even if the diameter φ1 of the opening 187 of the hole 185 is very small, it is possible to minimize the above-described problem in which the inspector may be unable to properly detect leakage of hydrogen gas due to a decrease in visibility.

(Elements)

Next, elements constituting a gas detection element according to an embodiment of the present invention will be described in detail. In the following, as an example, elements constituting the above-described first gas detection element 100 will be described. Therefore, the reference numerals indicated in FIG. 1 and FIG. 3 are used when referring to the elements.

(Backing 110)

As described above, the backing 110 serves to support upper-side elements such as the gas detection layer 120. However, the backing 110 may be omitted.

The backing 110 is transparent, and a change in color of the gas detection layer 120 is required to be visually checked from the side opposite to the gas detection layer 120, namely from the second side 104 of the first gas detection element 100.

Examples of a material of the backing 110 include polyimide, polyethylene (PE), polypropylene (PP), a fluorinated ethylene propylene copolymer (FEP), an ethylene tetrafluoroethylene copolymer (ETFE), polytetrafluoroethylene (PTFE), polyethylene terephthalate (PET), a tetrafluoroethylene-perfluoroalkyl vinyl ether copolymer, and polyvinylidene fluoride (PVDF).

The thickness of the backing 110 is not particularly limited. However, if the thickness of the backing 110 is very large, there is a possibility that a change in color of the gas detection layer 120 may be unclear. Therefore, the thickness of the backing 110 is in a range from 10 μm to 1000 μm, for example, in a range from 20 μm to 200 μm, and preferably, in a range from 25 μm to 100 μm.

Even if the backing 110 is used under ultraviolet radiation for a long period of time, it is preferable for the backing 110 not to deteriorate and not to change in color. If the backing 110 has such ultraviolet resistance, the first gas detection element 100 can be used outside for a long period of time. A period of time during which the color of the backing 110 does not change under ultraviolet radiation is, for example, one month or more, and preferably six months or more. The backing 110 may include weathering resistance agents such as an ultraviolet absorber and a light stabilizer.

(Gas Detection Layer 120)

As described above, the gas detection layer 120 includes the resin matrix 130 and the chemochromic pigment 135 added to the resin matrix 130. The chemochromic pigment 135 is preferably dispersed in the resin matrix 130.

The resin matrix 130 is not reactive with hydrogen gas and serves as a vehicle for holding the chemochromic pigment 135.

Further, the resin matrix 130 is configured not to significantly prevent diffusion of hydrogen gas. Otherwise, hydrogen gas may be prevented from reaching the chemochromic pigment 135, and hydrogen gas may be unable to be rapidly detected.

Further, the resin matrix 130 is formed of a material that allows a user to visually check a color change that occurs when the chemochromic pigment 135 contacts hydrogen gas.

Further, in order to provide the gas detection layer 120 with adhesiveness, the resin matrix 130 is formed of a material having adhesiveness.

Examples of the material of the resin matrix 130 include an acrylic resin, a silicone resin, a urethane resin, rubber, and an olefin. If the resin matrix 130 includes a silicone resin, the silicone resin may have a phenylmethyl group or a dimethyl group.

The chemochromic pigment 135 includes a material (hereinafter referred to as a "color-changing material") that changes in color by contacting hydrogen gas. For example, palladium oxide is known to change in color by contacting hydrogen gas. Therefore, the chemochromic pigment 135 may include palladium oxide as the color-changing material.

The color-changing material may irreversibly change in color upon contacting hydrogen gas.

The chemochromic pigment 135 may be in the form of particles.

As used herein, the term "particle" is not limited to a substance having an approximately spherical shape. The "particle" may have any shape such as a circular cylindrical shape, an angular cylindrical shape, a rod shape, a fibrous shape, a conical shape, a pyramidal shape, and a hemispherical shape.

Further, the chemochromic pigment 135 may include a noble metal catalyst to improve the reactivity with hydrogen gas. As the noble metal catalyst, the chemochromic pigment 135 may include noble metal, such as platinum and a platinum alloy, other than palladium. The noble metal catalyst is added to the chemochromic pigment 135, for example, by causing the noble metal to be carried or doped on the surface of the color-changing material. The noble metal may be formed of nanometer-order particles.

Further, the chemochromic pigment 135 may have a configuration in which the color-changing material is deposited on the surfaces of carrier particles. In addition, the noble metal catalyst may be carried by or doped into the color-changing material as described above. In the above configuration, the color-changing material covers at least part of the carrier particles.

The carrier particles may be formed of oxide such as titanium oxide.

The maximum size particles of the chemochromic pigment 135 may be in a range from 0.1 μm to 20 μm, and particularly, in a range from 0.2 μm to 10 μm. As used herein, the "maximum size" means the diameter of a particle if the particle has an approximately spherical shape or a hemispherical shape, and means the maximum length of a particle if the particle has any other shape such as an approximately circular cylindrical shape.

The mass ratio of the chemochromic pigment 135 to the resin matrix 130 is in a range from 1 wt % to 10 wt %.

The thickness of the gas detection layer 120 (substantially the same as the thickness of the resin matrix 130) is not particularly limited. For example, the thickness of the gas detection layer 120 may be in a range from 5 μm to 200 μm, preferably in a range from 10 μm to 100 μm, and more preferably in a range from 30 μm to 80 μm.

(Spacer 140)

The spacer 140 is formed of a material that is permeable to hydrogen gas. The term "permeable" includes "permeable in the thickness direction" of the spacer and "permeable in the plane direction" of the spacer 140. Further, the plane direction may be limited to the upper and lower surfaces of the spacer 140.

For example, the spacer may be formed of,
(1) paper made of pulp (including cardboard and kraft paper),
(2) a non-woven fabric or a woven fabric including fibers of an inorganic material such as glass, ceramic, or metal, or including fibers of a polymer material such as a synthetic resin,
(3) a thermal diffusion sheet including an inorganic material such as glass, ceramic, or metal, or including a polymer material such as a synthetic resin,
(4) a porous sheet including an inorganic material such as glass, ceramic, or metal, or including a polymer material such as a synthetic resin, or
(5) a foam having connected pores.

The thickness of the spacer 140 is not particularly limited. For example, the thickness of the spacer 140 may be in a range from 5 μm to 1000 μm, preferably in a range from 50 μm to 700 μm, and more preferably in a range from 60 μm to 400 μm.

Figure 4:
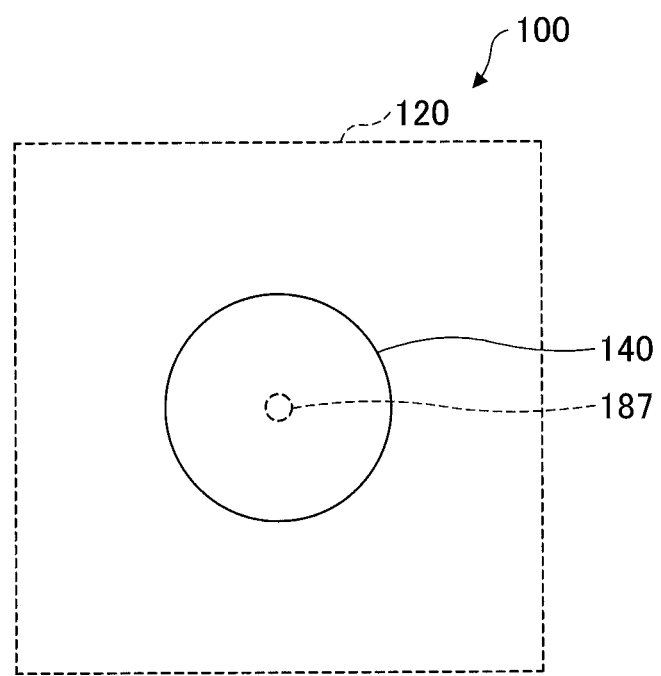
FIG. 4 is a top view schematically illustrating a spacer used in the gas detection element according to the embodiment of the present invention.

FIG. 4 is a schematic top view of an example of the first gas detection element 100. In FIG. 4, the backing 110 and the release liner 150 are omitted for clarification of explanation. Further, the gas detection layer 120 is indicated by a dashed line. Further, an example of the opening 187 of the inspection member 180 on which to place the first gas detection element 100 is also indicated by a dashed line, for reference.

In FIG. 4, when the first gas detection element 100 is used, the opening 187 of the inspection member 180 is positioned approximately at the center of the spacer 140. However, this is merely an example, and the relative positional relationship between the spacer 140 and the opening 187 is not particularly limited, as long as the opening 187 overlaps the spacer 140. Typically, the user of the first gas detection element 100 will use the first gas detection element 100 in such a manner that the opening 187 is positioned approximately at the center of the spacer 140.

Further, in FIG. 4, the spacer 140 has an approximately circular shape, and is located approximately at the center of the gas detection layer 120.

However, this is merely an example, and the shape of the spacer 140 and the relative positional relationship between the spacer 140 and the gas detection layer 120 are not particularly limited. For example, the spacer 140 may have an approximately elliptical shape, an approximately rectangular shape, an approximately trapezoid shape, or an approximately polygonal shape. Further, the spacer 140 may be in the form of a symbol and/or character, or may have a lattice shape. Further, a character may be printed on the spacer 140 such that the character appears when the color of the gas detection layer 120 changes.

Figure 5:
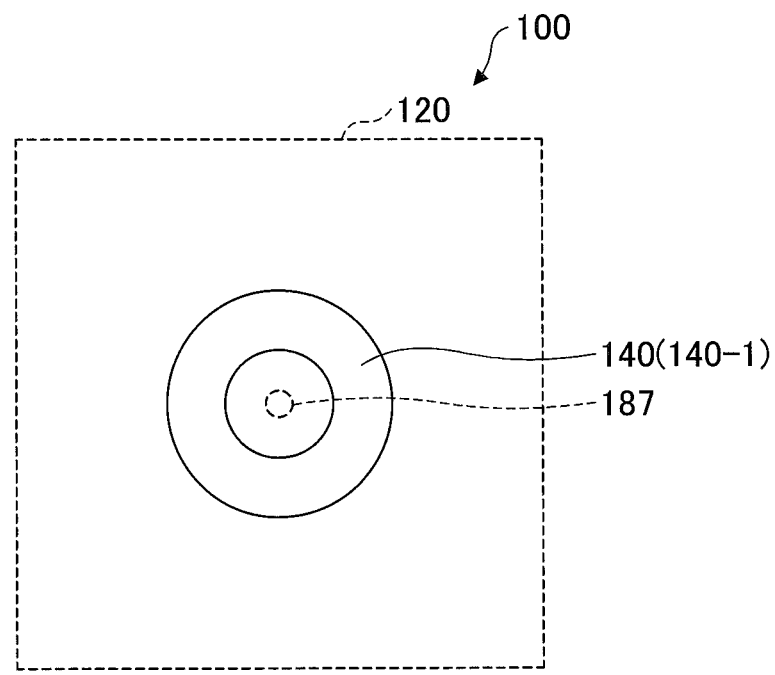
FIG. 5 is a top view schematically illustrating another spacer used in the gas detection element according to the embodiment of the present invention.
Figure 6:
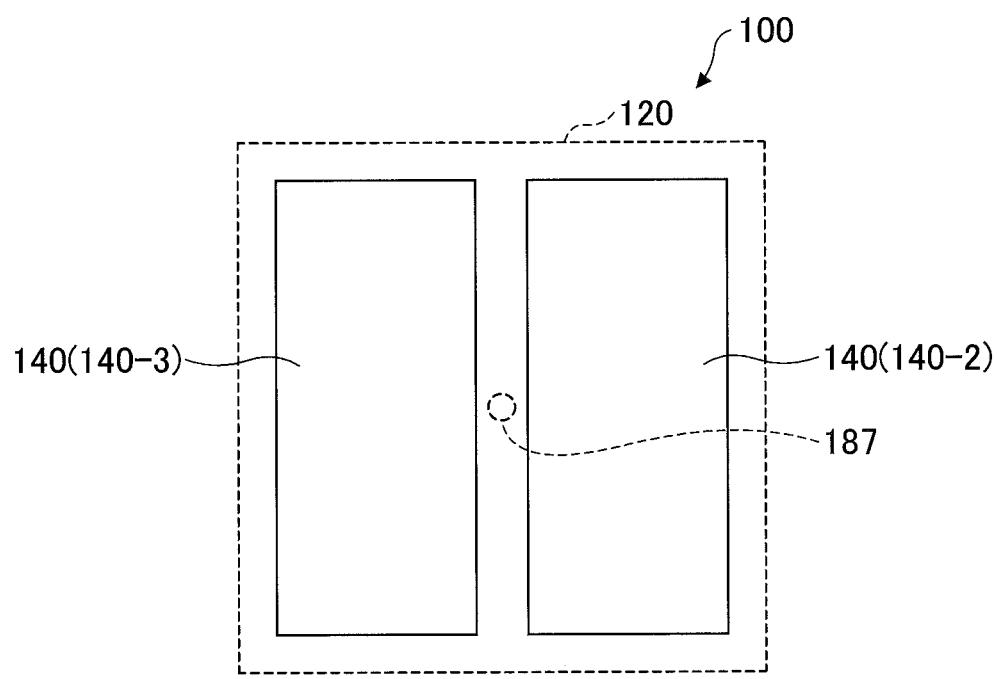
FIG. 6 is a top view schematically illustrating yet another spacer used in the gas detection element according to the embodiment of the present invention.

FIG. 5 and FIG. 6 schematically illustrate other example spacers used in the first gas detection element 100.

In the example of FIG. 5, a spacer 140-1 has a ring shape, and is positioned approximately at the center of the gas detection layer 120. When the gas detection layer 120 is used, the spacer 140-1 is placed such that a center hole of the ring-shaped spacer 140-1 surrounds the opening 187 of the inspection member 180. That is, a space is formed by the center hole of the ring-shaped spacer 140-1 above the opening 187.

In the example of FIG. 6, two spacers, spacer 140-2 and spacer 140-3, are used. The spacer 140-2 and spacer 140-3 have approximately rectangular shapes, and are spaced apart from each other by a predetermined distance. A gap between the spacer 140-2 and spacer 140-3 forms a region including the center of the gas detection layer 120. In other words, the spacer 140-2 and spacer 140-3 are placed such that the opening 187 of the inspection member 180 is positioned within the gap between the spacer 140-2 and spacer 140-3. Therefore, a space is formed between the spacer 140-2 and spacer 140-3 above the opening 187.

In the above examples, the peripheries of the spacers (140, 140-1, 140-2, and 140-3) are surrounded by the gas detection layer 120 in top view. However, these are merely examples, and at least parts of the end surfaces of the spacers (140, 140-1, 140-2, and 140-3) may be exposed to the outside. For example, in FIG. 6, the upper side and the lower side of each of the spacer 140-2 and the spacer 140-3 may extend to the end portions of the gas detection layer 120.

Figure 7:
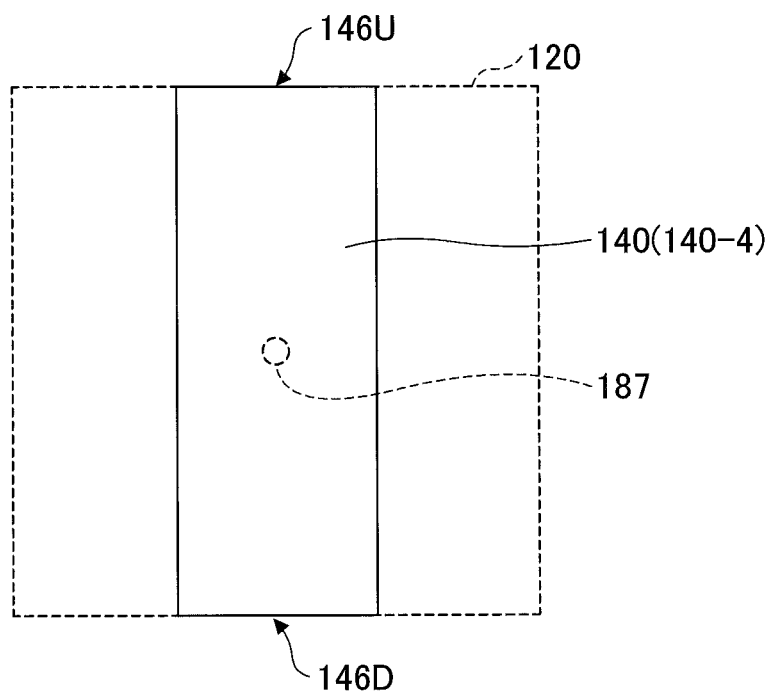
FIG. 7 is a top view schematically illustrating yet another spacer used in the gas detection element according to the embodiment of the present invention.

Alternatively, a spacer may be provided as illustrated in FIG. 7.

In the example of FIG. 7, a single spacer 140-4 having an approximately rectangular shape is provided approximately at the center of the gas detection layer 120 so as to cover the opening 187 in top view. Further, an upper side 146U and a lower side 146D of the spacer 140-4 extend to the respective end portions of the gas detection layer 120. However, one of the upper side 146U and the lower side 146D of the spacer 140-4 may extend to the corresponding end portion of the gas detection layer 120.

Figure 8:
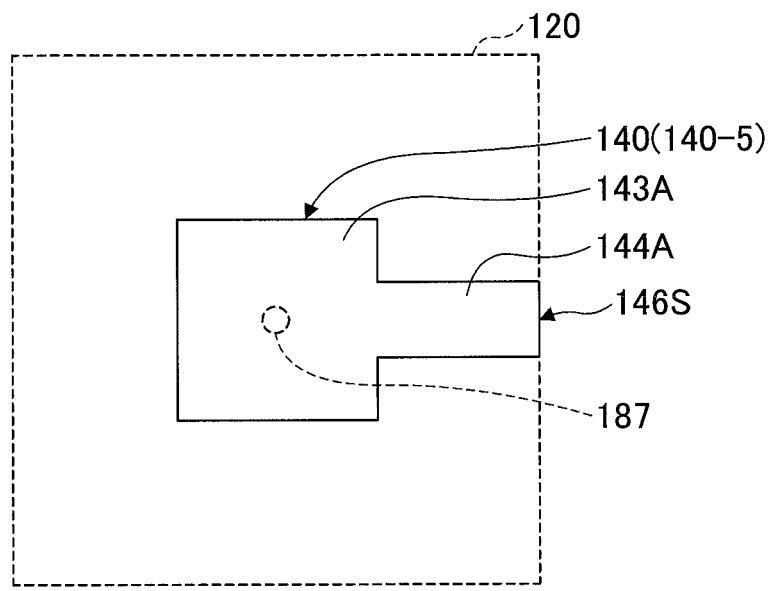
FIG. 8 is a top view schematically illustrating yet another spacer used in the gas detection element according to the embodiment of the present invention.
Figure 9:
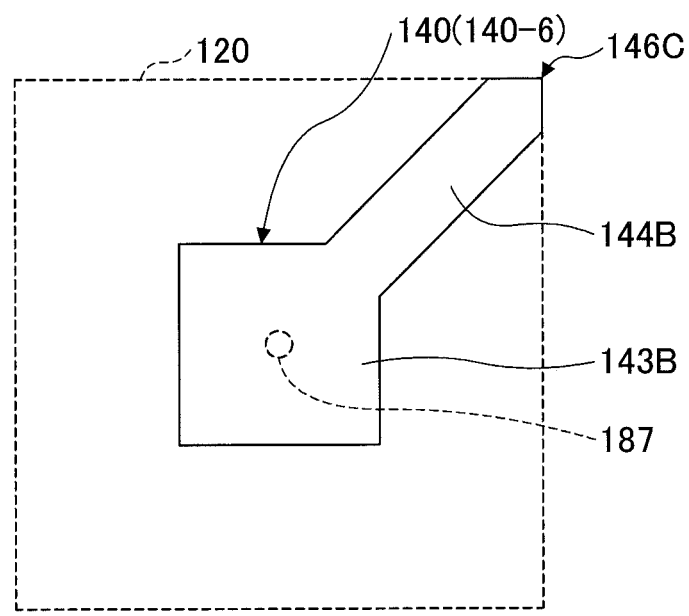
FIG. 9 is a top view schematically illustrating yet another spacer used in the gas detection element according to the embodiment of the present invention.

Further, if a part of a spacer may extend to the end portion of the gas detection layer 120 in top view, the spacer may have a configuration as illustrated in FIG. 8 or FIG. 9.

In the example illustrated in FIG. 8, a spacer 140-5 has a central rectangular portion 143A and an extending portion 144A in top view. The spacer 140-5 is provided approximately at the center of the gas detection layer 120 such that the central rectangular portion 143A covers the opening 187 in top view. Further, the extending portion 144A of the spacer 140-5 extends to the corresponding end portion (in the example of FIG. 8, to the side 146S) of the gas detection layer 120.

In the example illustrated in FIG. 9, a spacer 140-6 has a central rectangular portion 143B and an extending portion 144B in top view. The spacer 140-6 is provided approximately at the center of the gas detection layer 120 such that the central rectangular portion 143B covers the opening 187 in top view. Further, the extending portion 144B of the spacer 140-6 extends to the corresponding end portion (in the example of FIG. 8, to the corner 146C) of the gas detection layer 120.

With the configurations in which the spacers extend to the end portion(s) of the gas detection layer 120 in top view, as illustrated in FIG. 7 through FIG. 9, the release liner 150 can be readily peeled from the gas detection layer 120 when the first gas detection element 100 is used.

In addition to the above, various kinds of shapes and arrangements of spacers are contemplated by those skilled in the art.

In any of the configurations of the spacers illustrated in FIG. 4 through FIG. 7, when the area of the spacer 140 is defined as $S_s$, and the area of the gas detection layer 120 is defined as $S_g$ in top view, the ratio $S_s/S_g$ is preferably in a range of 0.02 to 0.9, more preferably in a range of 0.05 to 0.8, and even more preferably in a range of 0.1 to 0.7.

Note that the spacer 140 is not necessarily required to have the above-described functions from the beginning (before the first gas detection element 100 is attached to the inspection member 180 for use). For example, a layer that is not permeable to hydrogen may be provided on a part of the first surface 122 of the gas detection layer 120, and the layer is replaced with the spacer 140 at a later stage, for example, when the first gas detection element 100 is used.

For example, a layer capable of foaming may be preliminarily provided on the first surface 122 of the gas detection layer 120, and heat may be applied to the layer when the first gas detection element 100 is used, thereby causing the layer to foam and to become permeable to hydrogen gas.

In addition, the spacer 140 may have adhesiveness. In such a case, the spacer 140 may be used independently of other elements (such as the gas detection layer 120 and the backing 110), as will be described below.

In the above case, the spacer 140 is first placed at a desired position of the inspection member 180. Because the spacer 140 has adhesiveness, the spacer 140 can readily adhere to the desired position of the inspection member 180. Then, at a desired timing, the gas detection layer 120 (and the backing 110, if provided) is placed on the inspection member 180 so as to cover the spacer 140.

In such a manner, the gas detection element according to the embodiment of the present invention may be practically configured for the first time when actual gas detection is performed.

The spacer 140 used as described above is required to have adhesion to the inspection member 180. Therefore, the spacer 140 may include multiple layers.

Figure 10:
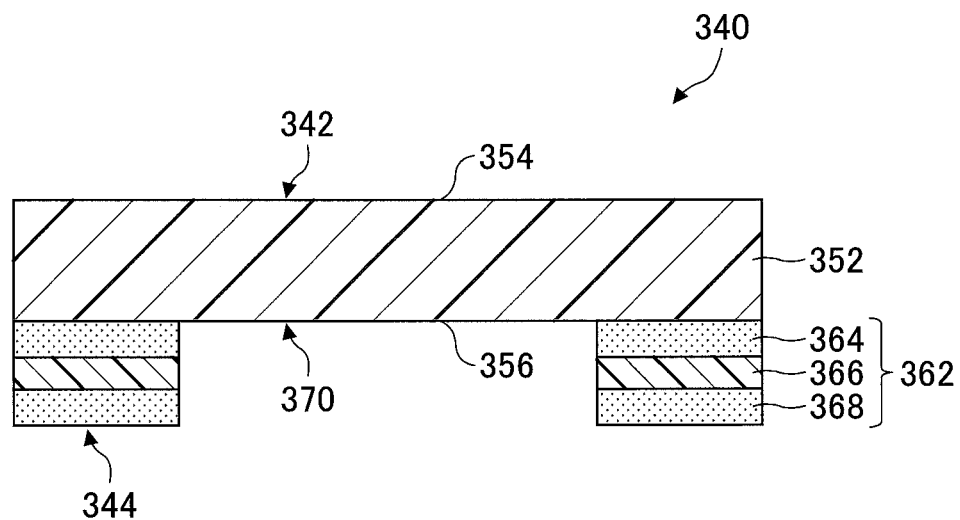
FIG. 10 is a cross-sectional view schematically illustrating an example of a multilayer spacer used in the gas detection element according to the embodiment of the present invention.

FIG. 10 is a cross-section view schematically illustrating an example of a spacer 340 (hereinafter referred to as a "multilayer spacer") having a structure in which multiple layers are stacked.

As illustrated in FIG. 10, the multilayer spacer 340 has a body layer 352 and an adhesive layer 362. The body layer 352 has a first surface 354 and a second surface 356. The adhesive layer 362 is provided on the second surface 356 of the body layer 352.

Further, the multilayer spacer 340 has a first side 342 and a second side 344. The first side 342 of the multilayer spacer 340 is the first surface 354 side of the body layer 352, and the second side 344 of the multilayer spacer 340 is the adhesive layer 362 side. When the multilayer spacer 340 is actually used, the first side 342 of the multilayer spacer 340 faces the gas detection layer 120, and the second side 344 of the multilayer spacer 340 faces the inspection member 180.

The body layer 352 may be formed of a material permeable to hydrogen gas as described in (1) to (5) above. Alternatively, the body layer 352 may be formed of a non-porous resin.

The thickness of the body layer 352 is not particularly limited. For example, the thickness of the body layer 352 may be in a range of 2 μm to 1000 μm.

The adhesive layer 362 is disposed to provide the body layer 352 with adhesiveness.

The adhesive layer 362 may be a single layer or may have a plurality of layers. For example, in the example illustrated in FIG. 10, the adhesive layer 362 has three layers; a first layer 364, the second layer 366, and the third layer 368 in order of proximity to the body layer 352.

The first layer 364 has adhesiveness, and is used to bond the layers formed on both sides of the first layer 364 to each other. For example, in the example illustrated in FIG. 10, the first layer 364 serves to bond the body layer 352 and the second layer 366 to each other.

The third layer 368 has a similar function to that of the first layer 364. Namely, the third layer 368 has adhesiveness, and serves to bond the second layer 366 and the inspection member to each other.

The second layer 366 is used to provide the adhesive layer 362 with stiffness.

The first layer 364 may be formed of, for example, an acrylic resin, a silicone resin, a urethane resin, rubber, or an olefin. When the first layer 364 includes a silicone resin, the silicone resin may have a phenylmethyl group or a dimethyl group.

Further, the first layer 364 may have a thickness of, for example, 1 μm to 200 μm. The thickness of the first layer 364 is preferably in a range of 5 μm to 100 μm, and more preferably in a range of 10 μm to 60 μm.

The third layer 368 has the same configuration as that of the first layer 364 described above.

The second layer 366 may be formed of polyimide, polyethylene (PE), polypropylene (PP), a fluorinated ethylene propylene copolymer (FEP), an ethylene tetrafluoroethylene copolymer (ETFE), polytetrafluoroethylene (PTFE), polyethylene terephthalate (PET), a tetrafluoroethylene-perfluoroalkyl vinyl ether copolymer (PFA), or polyvinylidene fluoride (PVDF).

The thickness of the second layer 366 is, for example, in a range of 1 μm to 100 μm, preferably in a range of 5 μm to 75 μm, and more preferably in a range of 10 μm to 50 μm.

If the adhesive layer 362 is a single layer, the above description of the first layer 364 (or the third layer 368) is regarded as the configuration of the adhesive layer 362, except that the thickness of the adhesive layer 362 may be adjusted to 3 μm to 500 μm, for example.

In the example illustrated in FIG. 10, the adhesive layer 362 is not provided on the entire second surface 356 of the body layer 352. Namely, the adhesive layer 362 is partially provided on the second surface 356 of the body layer 352. As a result, a non-adhesive region 370, where the adhesive layer 362 is not provided, is present on the second surface 356 of the body layer 352.

This is to prevent the adhesive layer 362 from blocking the flow of hydrogen gas into the body layer 352. However, for example, if the adhesive layer 362 is significantly thin, and does not block the flow of hydrogen gas into the body layer 352, the adhesive layer 362 may be provided on the entire second surface 356 of the body layer 352.

When the multilayer spacer 340 is used, the multilayer spacer 340 is placed on the inspection member 180, such that the second side 344 of the multilayer spacer 340, namely the adhesive layer 362 adheres to the inspection member 180.

Note that when the multilayer spacer 340 is prepared, the body layer 352 and the adhesive layer 362 are not necessarily required to be integrally formed. For example, only the adhesive layer 362 of the multilayer spacer 340 may be first disposed on the inspection member 180, and then, the body layer 352 of the multilayer spacer 340 may be disposed on the adhesive layer 362 to complete the multilayer spacer 340.

Subsequently, the rest (such as the gas detection layer 120 and the backing 110) of the gas detection element according to the embodiment of the present embodiment is placed on the first side 342 of the multilayer spacer 340. Accordingly, the gas detection element according to the embodiment of the present embodiment is provided.

(Release Liner 150)

The release liner 150 is not particularly limited, and any general release paper may be used. For example, it is possible to use a release liner having a release-treated layer on the surface of a liner substrate such as a resin film (PET, for example) or paper, or use a release liner made of a low adhesive material, such as a fluorine-based polymer (such as polytetrafluoroethylene) or a polyolefin-based resin (such as PE and PP). The above-described release-treated layer may be formed by subjecting the liner substrate to surface treatment using a release treatment agent, such as a silicone-based, long-chain alkyl-based, fluorine-based, or molybdenum sulfide release treatment agent. The thickness (total thickness) of the release liner 150 is not particularly limited; however, in terms of release workability, handleability, and strength, the thickness of the release liner 150 is preferably approximately 10 to 500 μm (15 μm to 100 μm, for example).

Further, the release liner 150 may have various releasing means that allow the release liner 150 to be readily removed when the first gas detection element 100 is used. Such a releasing means may be the above-described protruding portion 154. Alternatively, the releasing means may be one or more cut lines formed on a part of the surface of the release liner 150. The release liner 150 can be separated along the one or more cut lines. Thus, the release liner 150 can be readily removed. In this case, some portions of the release liner 150 to be separated may overlap each other.

(First Gas Detection Element 100)

When the first gas detection element 100 is used for actual hydrogen gas detection, a color change $\Delta L^*$ is preferably greater than or equal to 10 in an area of 5 cm$^2$.

The color change $\Delta L^*$ can be evaluated by the following method.

By using a colorimeter, the chromaticity of a standard whiteboard is measured. Furthermore, the chromaticity of the gas detection element before use is measured. Note that the chromaticity is expressed by the lightness index of the $L^*a^*b^*$ color system (CIE 1976). The absolute value of the difference in the measured chromaticity between the standard whiteboard and the gas detection element before use is obtained as $\Delta L_{initial}$.

Similarly, the chromaticity of the gas detection element after use is measured. The absolute value of the difference in the measured chromaticity between the standard whiteboard and the gas detection element after use is obtained as $\Delta L_{final}$.

From the above results, the color change $\Delta L^*$ of the gas detection element can be evaluated by $\Delta L^* = |\Delta L_{initial} - \Delta L_{final}|$.

The form of the first gas detection element 100 is not particularly limited.

The first gas detection element 100 may be in the form of a patch (small piece), or may be in the form of a strip (hereinafter referred to as a "cut piece").

If the first gas detection element 100 is in the form of a cut piece, the first gas detection element 100 is not required to be cut by the worker each time the first gas detection element 100 is used, unlike the form of a tape. Accordingly, it is possible to facilitate the work to attach the first gas detection element 100 to the inspection member 180.

If the first gas detection element 100 is in the form of a patch, the first gas detection element 100 may have any shape such as an approximately circular shape, an approximately elliptical shape, an approximately triangle shape, an approximately rectangular shape, or an approximately polygonal shape. In the case of an approximately circular shape, the diameter of the approximately circular shape may be in a range of 2 mm to 30 mm, and particularly in a range of 3 mm to 10 mm. Further, in the case of an approximately rectangular shape, the length of the longest side of the approximately rectangular shape may be in a range of 2 mm to 30 mm, and particularly in a range of 3 mm to 25 mm.

If the first gas detection element 100 is in the form of a patch, the first gas detection element 100 may be provided as a laminate in which multiple first gas detection elements 100 are stacked in the thickness direction.

Figure 11:
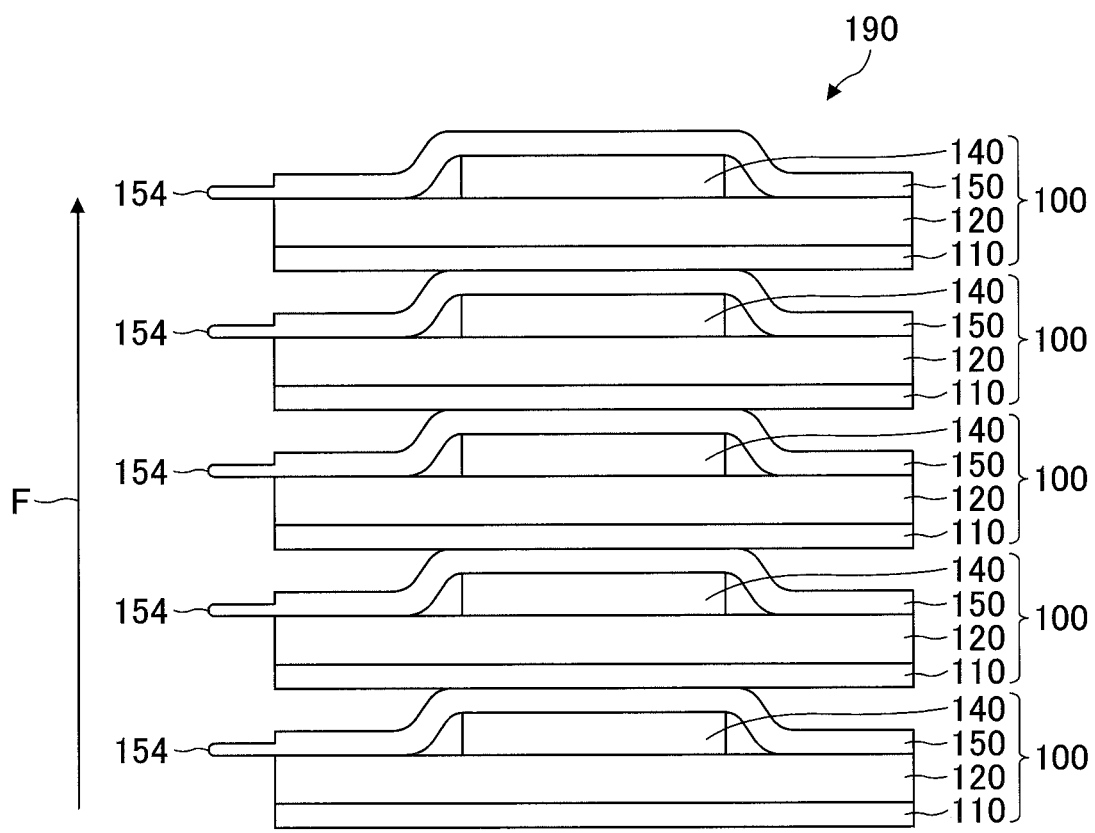
FIG. 11 is a diagram schematically illustrating an example of a laminate in which multiple gas detection elements are stacked.

FIG. 11 schematically illustrates an example of a laminate 190 in which multiple first gas detection elements 100 are sequentially stacked.

As illustrated in FIG. 11, the laminate 190 is formed by stacking five first gas detection elements 100 in the thickness direction (in the direction indicated by an arrow F). However, this is merely an example, and the number of stacked first gas detection elements (the number of times first gas detection elements are stacked) may be two, three, four, six, seven, eight, or nine or more.

Further, in the example illustrated in FIG. 11, the first gas detection elements 100 each have the configuration illustrated in FIG. 1. However, in the first gas detection elements 100, backings 110 or release liners 150 may be omitted.

However, it is preferable not to omit a backing 110 of the bottom first gas detection element 100 (upstream side of the arrow F) and a release liner 150 of the top first gas detection element 100 (downstream side of the arrow F). This is to prevent a corresponding gas detection layer 120 and a corresponding spacer 140 from being exposed.

In order to use one of the first gas detection elements 100, the top or the bottom first gas detection element 100 is separated from the laminate 190. At this time, the first gas detection element 100 may be separated by holding up or down the protruding portion 154 provided on the release liner 150 of the first gas detection element 100.

If the first gas detection element 100 is in the form of a strip, the length LL in the longitudinal direction of the first gas detection element 100 may be selected to conform to the circumferential dimension of a circular-shaped inspection member, such as a flange or a pipe. For example, the length LL in the longitudinal direction of the first gas detection element 100 may range from 250 mm to 600 mm.

Figure 12:
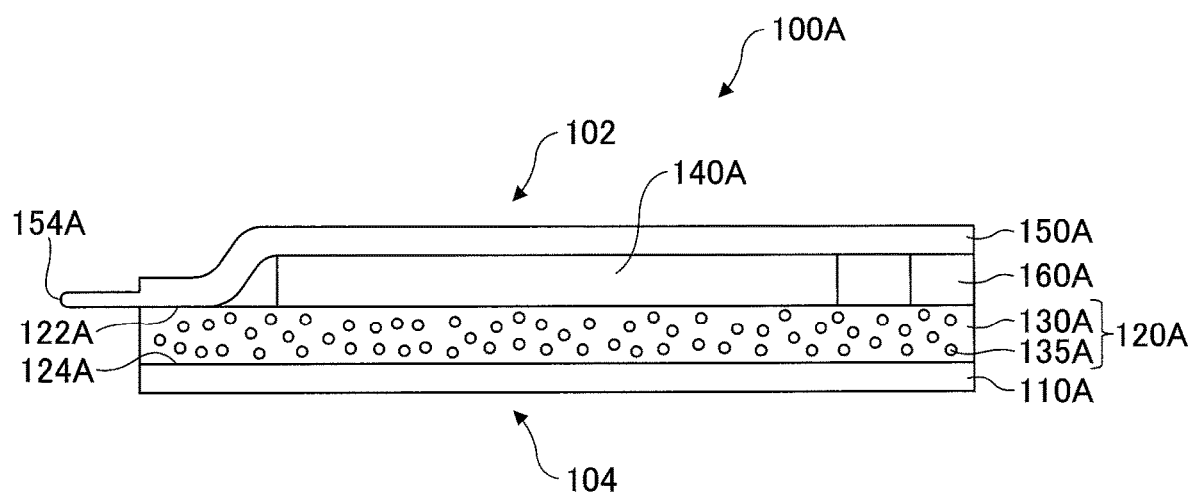
FIG. 12 is a cross-sectional view schematically illustrating an example of a gas detection element in the form of a strip according to an embodiment of the present invention.

FIG. 12 schematically illustrates a cross-section of a first gas detection element in the form of a strip.

As illustrated in FIG. 12, a first gas detection element 100A in the form of a strip includes a backing 110A, a gas detection layer 120A, a spacer 140A, and a release liner 150A. As described above, one or both of the backing 110A and the release liner 150A may be omitted.

The gas detection layer 120A has a first surface 122A and a second surface 124A. The first surface 122A of the gas detection layer 120A is a surface farther from the backing 110A, and the second surface 124A is a surface nearer to the backing 110A.

The gas detection layer 120A includes a resin matrix 130A and a chemochromic pigment 135A added to the resin matrix 130A. Further, the gas detection layer 120 has adhesiveness.

The configurations of the above elements are the same as those described above.

The first gas detection element 100A in the form of the strip has a tab portion 160A at one end in the longitudinal direction of the first surface 122A of the gas detection layer 120A.

The tab portion 160A is composed of, for example, paper, a plastic resin, a film, or a release liner. The tab portion 160A may be a non-adhesive material.

The tab portion 160A is not necessarily required to be provided on the first surface 122A of the gas detection layer 120A. For example, the tab portion 160A may be formed by removing adhesiveness at one end of the gas detection layer 120A. Alternatively, the tab portion 160A may be formed by causing one end of the backing 110A to extend outward relative to the other members (particularly, the gas detection layer 120A).

By providing the tab portion 160A, the first gas detection element 100A can be readily removed from the inspection member 180 after the first gas detection element 100A is attached to the inspection member 180. That is, when the first gas detection element 100A is removed from the inspection member 180 after use, the first gas detection element 100A can be separated from the inspection member 180 by holding the tab portion 160A.

The tab portion 160A may also be applied to a first gas detection element 100 in the form of a patch.

(Another Gas Detection Element According to One Embodiment of Present Invention)

Next, referring to FIG. 13, another gas detection element according to an embodiment of the present invention will be described.

Figure 13:
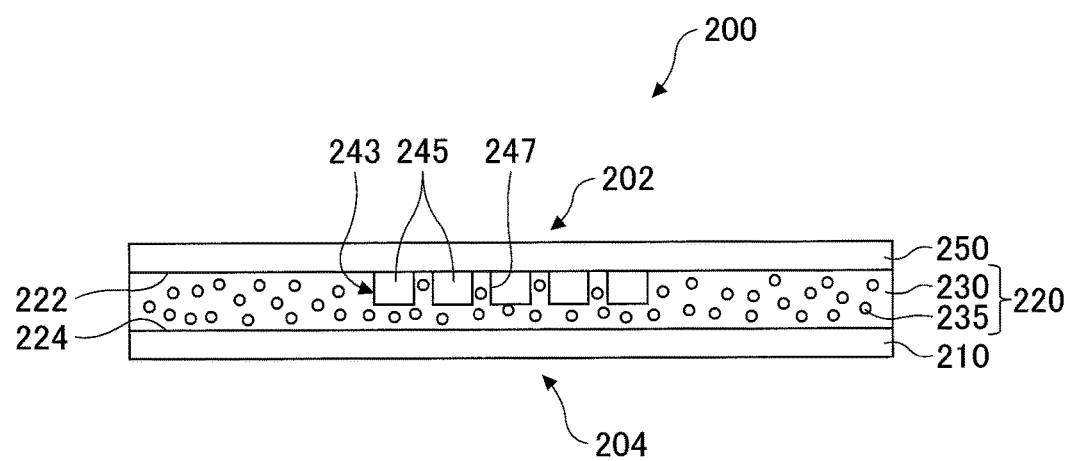
FIG. 13 is a schematic cross-sectional view of a configuration example of another gas detection element according to an embodiment of the present invention.

FIG. 13 schematically illustrates an example configuration of another gas detection element (hereinafter referred to as a "second gas detection element") according to an embodiment of the present invention.

As illustrated in FIG. 13, a second gas detection element 200 has a first side 202 and a second side 204.

Further, the second gas detection element 200 includes a backing 210, a gas detection layer 220, and a release liner 250. The release liner 250 constitutes the first side 202 of the second gas detection element 200. The backing 210 constitutes the second side 204 of the second gas detection element 200. However, one or both of the backing 210 and the release liner 250 may be omitted.

Note that the backing 210 and the release liner 250 have similar functions to those of the backing 110 and the release liner 150 of the above-described first gas detection element 100, respectively, and thus, a description thereof will be omitted.

The gas detection layer 220 has a first surface 222 and a second surface 224. The first surface 222 of the gas detection layer 220 is a surface farther from the backing 210, and the second surface 224 is a surface nearer to the backing 210.

The gas detection layer 220 includes a resin matrix 230 and a chemochromic pigment 235 added to the resin matrix 230.

The chemochromic pigment 235 may include a material, for example palladium oxide, that changes in color by contacting hydrogen gas.

The gas detection layer 220 has adhesiveness.

Although not illustrated in FIG. 13, the second gas detection element 200 may further include an adhesion layer (an undercoat layer) between the backing 210 and the gas detection layer 220.

The gas detection layer 220 has a surface processing portion 243 at approximately the center of the first surface 222. The surface processing portion 243 is provided on the first surface 222 of the gas detection layer 220 to form spaces to be filled with hydrogen gas.

For example, in the example illustrated in FIG. 13, the surface processing portion 243 is formed by a plurality of recessed portions 245, which form spaces. The adjacent recessed portions 245 are separated from each other by thin wall portions 247.

Although it is not clear from FIG. 13, the shape in the depth direction of each of the recessed portions 245 forming the surface processing portion 243 is not particularly limited, and the shape of each of the recessed portions 245 is not particularly limited.

Figure 14:
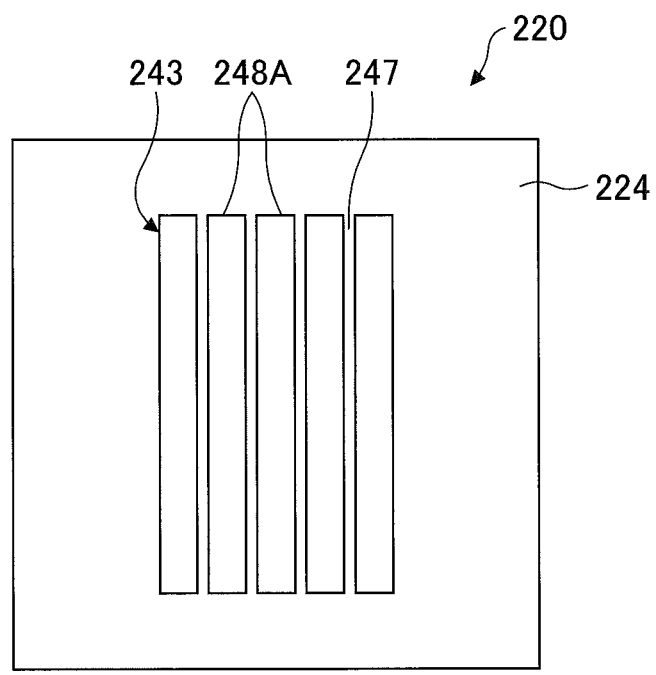
FIG. 14 is a schematic top view of a first surface of a gas detection layer of the other gas detection element according to the embodiment of the present invention.
Figure 15:
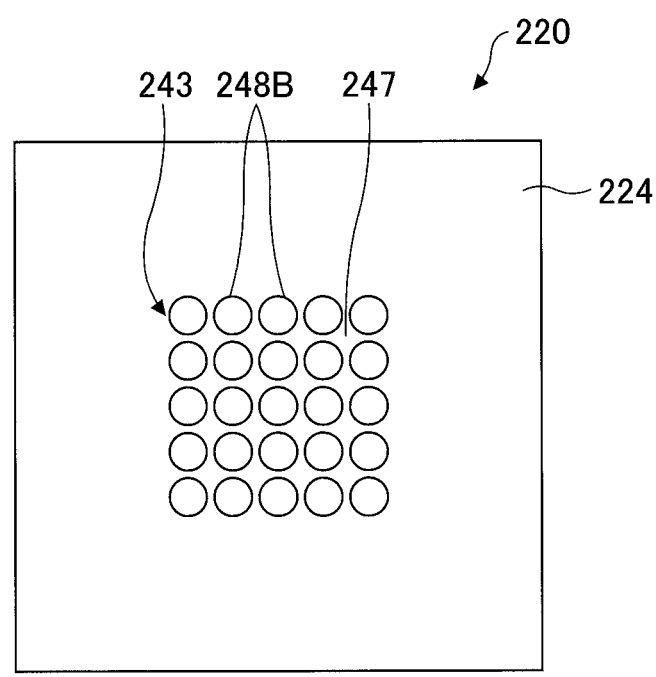
FIG. 15 is a schematic top view of the first surface of the gas detection layer of the other gas detection element according to the embodiment of the present invention.

For example, each of the recessed portions 245 may be formed in a shape as illustrated in FIG. 14 or FIG. 15.

In the example of FIG. 14, the surface processing portion 243 has a plurality of stripe-shaped grooves 248A that are separated from each other via the thin wall portions 247. Namely, the recessed portions 245 illustrated in FIG. 13 are formed by the grooves 248A.

In the example illustrated in FIG. 15, the surface processing portion 243 has a plurality of disk-shaped recesses 248B that are separated from each other via the thin wall portions 247. Namely, the recessed portions 245 illustrated in FIG. 13 are formed by the recesses 248B.

In addition to the above, various shapes are contemplated for the recessed portions 245.

The surface processing portion 243 can be formed by, for example, embossing the first surface 222 of the gas detection layer 220.

Next, an application example of the second gas detection element 200 will be described with reference to FIG. 16.

Figure 16:
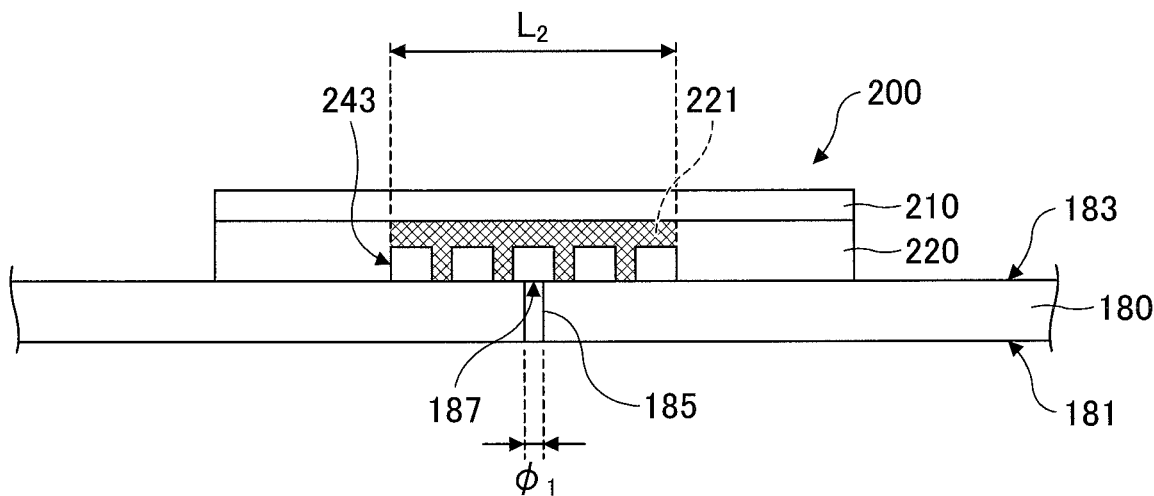
FIG. 16 is a cross-sectional view schematically illustrating an application example of the other gas detection element according to the embodiment of the present invention.

FIG. 16 schematically illustrates an example in which the second gas detection element 200 is placed on the inspection member 180. For ease of illustration, the chemochromic pigment 235 included in the gas detection layer 220 is not depicted in FIG. 16.

When the second gas detection element 200 is actually used for the inspection member 180, the release liner 250 is removed from the second gas detection element 200 first. At this time, a protruding portion (not illustrated in FIG. 13) provided on the release liner 150 may be used.

Next, the second gas detection element 200 is attached to the inspection member 180. At this time, the second gas detection element 200 is attached in such a manner that the first surface 222 of the gas detection layer 220, exposed by the removal of the release liner 250, is brought into contact with the inspection member 180.

The second gas detection element 200 is preferably placed in such a manner that any of the recessed portions 245 of the surface processing portion 243 (that is, a space in the gas detection layer 220) is positioned over the opening 187 of the inspection member 180. In this manner, evaluation of hydrogen gas leakage can be promptly performed, as compared to when any of the wall portions 247 of the surface processing portion 243 is positioned over the opening 187.

However, if the wall portions 247 of the surface processing portion 243 are sufficiently thin, the second gas detection element 200 may be placed without much considering the above-described conditions.

Accordingly, the gas detection layer 220 can be placed on the inspection member 180 as illustrated in the example of FIG. 16. Because the gas detection layer 220 has adhesiveness, the gas detection layer 220 is fixed onto the inspection member 180 by the adhesion of the gas detection layer 220.

In this state, if hydrogen gas leaks from a hole 185 of the inspection member 180, the surface processing portion 243 of the second gas detection element 200, particularly the recessed portions 245 are filled with the leaked hydrogen gas. Subsequently, the hydrogen gas is relatively readily diffused throughout the surface processing portion 243 via the thin wall portions 247 and the recessed portions 245.

As a result, in the second surface 224 of the gas detection layer 220, a region that contacts the hydrogen gas significantly increases. Thus, a large color change region 221 can be obtained. For example, in the example illustrated in FIG. 16, as compared to the diameter φ1 of the opening 187 of the hole 185, a color change region 221 having a sufficiently large dimension L2 can be obtained.

Accordingly, in the second gas detection element 200, even if the opening 187 of the hole 185 is very small, it is possible to minimize the above-described problem in which the inspector may be unable to properly detect leakage of hydrogen gas due to a decrease in visibility.

In the second gas detection element 200, the surface processing portion 243 illustrated in FIG. 13 through FIG. 15 is merely an example. The surface processing portion 243 may be in any form as long as the surface processing portion 243 has a space to be filled with hydrogen gas.

For example, in FIG. 13, the surface processing portion 243 may be formed by a single recessed portion 245. Alternatively, the surface processing portion 243 may be one or more projecting portions formed on the second surface 224. Alternatively, the surface processing portion 243 may be a combination of one or more recessed portions and one or more projecting portions.

Other various configurations may be contemplated.

(Method for Manufacturing Gas Detection Element According to Embodiment of Present Invention)

Next, referring to FIG. 17, a method for manufacturing a gas detection element having features as described above according to an embodiment of the present invention will be described.

Figure 17:
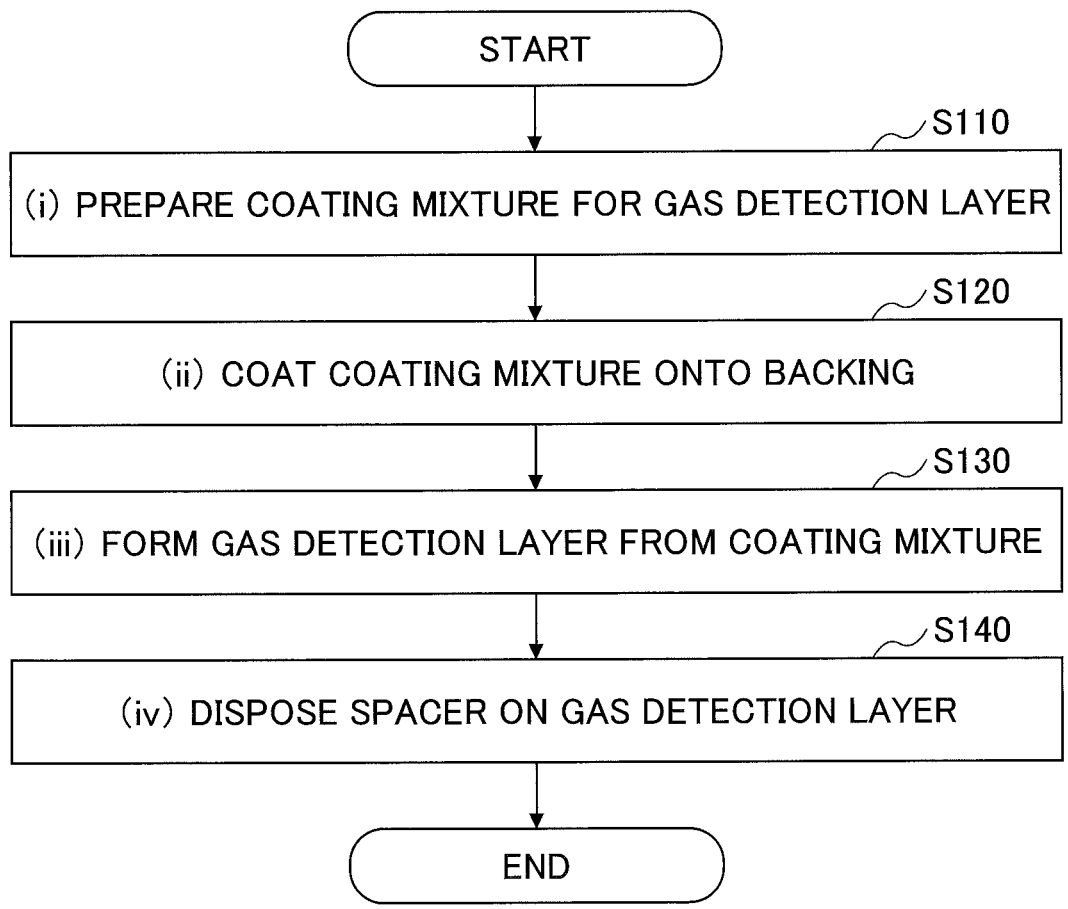
FIG. 17 is a flowchart schematically illustrating a method for manufacturing a gas detection element according to an embodiment of the present invention.

FIG. 17 schematically illustrates an example flowchart of a method for manufacturing a gas detection element according to an embodiment of the present invention.

As illustrated in FIG. 17, a method for manufacturing a gas detection element (hereinafter referred to as a "first manufacturing method") according to an embodiment of the present invention includes:

(1) a step (S110) of preparing a coating mixture for a gas detection layer;

(ii) a step (S120) of coating the coating mixture onto a backing;

(iii) a step (S130) of forming a gas detection layer from the coating mixture; and (iv) a step (S140) of disposing a spacer on the gas detection layer.

In the following, each step will be described. As an example, the method for manufacturing the above-described first gas detection element 100 will be described. Therefore, the reference numerals indicated in FIG. 1 are used when referring to the elements.

(Step S110)

First, a coating mixture, which is obtained as the gas detection layer 120, is prepared.

The coating mixture is produced by, for example, mixing a dispersion liquid including a chemochromic pigment with a treatment liquid, which is obtained as the resin matrix 130 of the gas detection layer 120.

In the following, an example of a method for preparing the dispersion liquid including the chemochromic pigment and an example of a method for preparing the treatment liquid will be described.

(Method for Preparing Dispersion Liquid)

For example, the dispersion liquid including the chemochromic pigment will be prepared as follows.

First, a palladium salt is added to a slurry including carrier particles, and is sufficiently mixed. The slurry may include water. Further, the carrier particles may be titanium dioxide. The palladium salt may be, for example, chloride, sulfide, nitrate, or acetate. The palladium salt in the form of a solution may be added to the slurry.

The slurry is then neutralized by adding an acid or an alkali. During the neutralization reaction, fine palladium oxide particles are deposited onto the surfaces of the carrier particles, thereby obtaining composite particles with palladium oxide deposited on the surface.

A noble metal such as platinum (other than palladium) may be further deposited on the surfaces of the obtained composite particles. If platinum is deposited on the surfaces of the composite particles, a platinum compound is added to the slurry of the composite particles. A solvent for the slurry may be an organic solvent such as ethanol. The platinum compound may be, for example, a solution including chloride, sulfide, nitrate, or acetate.

By thoroughly stirring the above mixture, a chemochromic pigment including platinum deposited on the surfaces of the composite particles can be obtained.

The chemochromic pigment is suspended in an organic solvent such as ketone to obtain a dispersion liquid. The organic solvent may be butyl acetate, methyl ethyl ketone, or methyl isobutyl ketone.

(Method for Preparing Treatment Liquid))

The treatment liquid includes, for example, siloxane precursor and an initiator. The treatment liquid may further include a solvent.

The siloxane precursor may include an organosiloxane and/or an oligosiloxane.

The organosiloxane may be a monomer or polymer (linear or cyclic) methyl siloxane.

The oligosiloxane may have a silicone resin such as an MQ resin.

The initiator may include a peroxide, such as benzoyl peroxide or 2,4-dichlorobenzoyl peroxide.

The initiator may be added to the treatment liquid at a concentration ranging from 0.1 wt % to 3.0 wt %.

The solvent may include an alkylbenzene such as methyl benzene or ethyl benzene. The methyl benzene may be xylene or toluene. The xylene may include 1,2-dimethylbenzene, 1,3-dimethylbenzene, 1,4-dimethylbenzene (p-xylene), or any combination thereof.

A coating mixture is prepared by mixing the above-described dispersion liquid and the treatment liquid.

(Step S120)

Next, the coating mixture prepared in step S110 is coated onto the surface of the backing 110.

A method for coating the coating mixture is not particularly limited. The coating mixture may be coated onto the surface of the backing 110 by any method such as brush coating, spray coating, or printing.

In order to increase the adhesion between the gas detection layer 120 to be obtained in step S130 and the backing 110, an adhesion layer may be preliminarily disposed on the surface of the backing 110.

The adhesion layer may be, for example, a phenylmethyl-based resin.

(Step S130)

Next, a gas detection layer is formed from the coating mixture coated onto the backing 110.

For example, after the solvent included in the coating mixture is removed, the coating mixture is cured to obtain the gas detection layer 120 that includes the resin matrix 130, which is a siloxane polymer matrix, and the chemochromic pigment 135 dispersed in the resin matrix 130. The heating temperature for removing the solvent is, for example, in a range of 25° C. to 100° C.

The treatment liquid may be heated to a temperature sufficient to activate the initiator. Activating the initiator causes the precursor to be crosslinked, thereby forming the resin matrix 130 of the gas detection layer 120.

The heating temperature for activating the initiator may be in a range of 120° C. to 250° C.

(Step S140)

Next, the spacer 140 is disposed on the gas detection layer 120 formed in step S130.

A method for disposing the spacer 140 is not particularly limited. For example, the spacer 140 may be manually disposed on the gas detection layer 120.

Further, the material of the spacer is not limited to those described above, and any material may be used as long as the material is permeable to hydrogen gas.

As described above, the spacer 140 is not necessarily required to have hydrogen gas permeability at the time when the spacer 140 is disposed. For example, a layer capable of foaming may be preliminarily provided on the detection layer 120. Then, when the first gas detection element 100 is used, the spacer 140 may be formed by applying heat to the layer to cause the layer to foam.

With the above steps, the first gas detection element 100 as illustrated in FIG. 1 can be manufactured. The first manufacturing method is merely an example, and the first gas detection element 100 may be manufactured by any other manufacturing method.

For example, as described above, the first gas detection element 100 may be configured by first disposing the spacer 140 on the inspection member 180, and then disposing other elements such as the gas detection layer 120 on the spacer 140.

Although the configuration examples and features of the first and second gas detection elements 100, 100A, and 200 capable of detecting hydrogen gas have been described above, it will be apparent to those skilled in the art that the gas detection elements according to the present invention may be configured to detect any reducing gas other than hydrogen gas.

Accordingly, by appropriately selecting a color-changing material included in the chemochromic pigment of the gas detection layer, a gas detection element sensitive to various reducing gases can be provided.

EXAMPLES

Examples of the present invention will be described below.

Example 1

A gas detection element was manufactured by the following method.

The gas detection element had a configuration including a backing, an undercoat layer, a gas detection layer including a chemochromic pigment, and a spacer in the stated order.
(Preparing Backing and Spacer)

As the backing, polyimide (Kapton) (Dupont High Performance Films Circleville, Ohio, USA) having a thickness of 25 μm was prepared.

As the spacer, a non-woven fabric (HOP-60HCF(170); Hirose Paper Mfg Co., Ltd.) with 10 mm in length and 10 mm in width was prepared. The thickness of the non-woven fabric is approximately 164 μm.

The Gurley method was used to evaluate the air permeability of the spacer. For measurement, a Gurley type densometer (No. 323-AUTO; manufactured by Yasuda Seiki) was used, and the measurement was performed in accordance with JIS P8117.

As a result of the measurement, the air permeability of the spacer was 0.06 sec/100 cm$^3$.
(Coating Liquid for Undercoat Layer)

A coating liquid for the undercoat layer was prepared by the following method.

A polysiloxane (SS4195A-D1: manufactured by Momentive) including 15.06 g of a phenylmethylsiloxy group was dissolved in 96.61 g of xylene at room temperature, and was then sufficiently stirred, to obtain a uniform solution. In the stirring state, 0.34 g of a cross-linking agent (SS4191B: manufactured by Momentive) was added to this solution, and the solution was further stirred for several minutes. Next, 0.567 g of an accelerator (SS4259c: manufactured by Momentive), and 0.567 g of a catalyst (SS4192C: manufactured by Momentive) were sequentially added, and the solution was stirred for several minutes. Accordingly, the coating liquid (hereinafter referred to as a "U-1") for the undercoat layer was obtained.
(Preparing Chemochromic Pigment)

Next, a chemochromic pigment was prepared by the following method.

A slurry of 2.5 g TiO$_2$ particles (an average particle size of less than 5 μm, rutile) in 100 mL of water was adjusted to pH 10.6 using an NaOH solution and stirred at 70° C. for one hour.

Next, 2.50 mL of a PdCl$_2$ solution (0.281 M) was added to the mixture, while maintaining the solution at pH 10.6 using an NaOH solution. Then, the pH of the mixture was adjusted to 8 using an HCl solution (3N).

Next, the mixture was stirred and heated for one hour. As a result, palladium oxide (PdO) was deposited onto the surfaces of the TiO$_2$ particles. The resulting solid particulates were filtered, washed, and then dried at 110° C. for 3 hours.

Accordingly, PdO/TiO$_2$ particles (hereinafter referred to as "C-1") including 3.3 wt % PdO was obtained.

In 100 mL of ethanol, 2.5 g of the obtained PdO/TiO$_2$ particles (C-1) was suspended to prepare a slurry, and 0.019 g of Na$_2$PtCl$_6$.6H$_2$O (manufactured by Aldrich) was added to the slurry. The pH of the slurry was then adjusted to 6 using NaOH.

Next, the slurry was sufficiently stirred by sonication. The resulting product was filtered, washed with ethanol, and then dried at room temperature.

Next, the product was subjected to heat treatment at 110° C. for 3 hours to obtain a chemochromic pigment with 0.26 wt % of Pt being carried (hereinafter referred to as "CC-1").
(Preparing Coating Mixture for Gas Detection Layer)

The chemochromic pigment CC-1 obtained by the above method was used to prepare a coating mixture for the gas detection layer as follows.

First, 2.39 g of the chemochromic pigment CC-1 was sufficiently dispersed in 10.4 g of methyl ethyl ketone to produce a dispersion liquid of the chemochromic pigment.

Next, 1.0 g of benzoyl peroxide (97%, Luperox (registered trademark) A98, Aldrich) was added to 10 g of toluene. The obtained solution was stirred for one minute, to completely dissolve the benzoyl peroxide.

Next, all of the solution and 18 g of toluene were added to 75 g of a siloxane precursor (PSA518, Momentive Performance Materials, Waterford, N.Y. USA), and stirred for three minutes. Accordingly, a treatment liquid including a silicone-based resin was produced.

Next, in the obtained treatment liquid, 12.79 g of the above-described dispersion liquid of the chemochromic pigment was added, and was sufficiently stirred until a uniform liquid was obtained.

Accordingly, a coating mixture (hereinafter referred to as "C-1") was obtained.
(Producing Gas Detection Element)

The gas detection element was produced as follows.

First, the coating liquid U-1 for the undercoat layer having a thickness of approximately 1 μm was coated on the backing, and then dried at 120° C. Accordingly, the undercoat layer was formed.

Next, a bar coater (SA-210, Tester Sangyo Co., Ltd.) was used to coat the undercoat layer with the coating mixture CM-1.

Next, the backing coated by the undercoat layer and the coating mixture CM-1 was dried at 25° C., to remove the solvent. Next, the backing was retained in an oven for 3 minutes at 177° C. Accordingly, the gas detection element was formed on the undercoat layer. The thickness of the gas detection layer was approximately 35 μm.

Next, an assembly including the backing, the undercoat layer, and the gas detection layer was cut into a size of 20 mm×20 mm.

Further, as the spacer, the above-described non-woven fabric was placed approximately at the center of the gas detection layer.

Accordingly, a patch-type gas detection element (hereinafter referred to as a "sample 1") was obtained.

Example 2

A patch-type gas detection element (hereinafter referred to as a "sample 2") was manufactured by a method similar to that of Example 1.

However, in Example 2, two non-woven fabrics were stacked and used as a spacer. Thus, the thickness of the spacer was 328 μm.

The air permeability of the spacer was measured by the above-described method. The air permeability of the spacer was 0.11 sec/100 cm$^3$.

Example 3

A gas detection element was manufactured by a method similar to that of Example 1.

However, in Example 3, a silicone-based thermal diffusion sheet (EX40015DS; manufactured by Dexerials Corporation) having a thickness of approximately 150 μm was used as a spacer.

Accordingly, a patch-type gas detection element (hereinafter referred to as a "sample 3") was obtained.

Example 4

A patch-type gas detection element (hereinafter referred to as a "sample 4") was manufactured by a method similar to that of Example 1.

However, in Example 4, a polytetrafluoroethylene (PTFE)-based porous sheet (NTF1131; manufactured by Nitto Denko Corporation) was used as a spacer. The thickness of the porous sheet was 70 μm.

The air permeability of the spacer was measured by the above-described method. The air permeability of the spacer was 4.1 sec/100 cm$^3$.

Example 5

A patch-type gas detection element (hereinafter referred to as a "sample 5") was manufactured by a method similar to that of Example 4.

However, in Example 5, a polytetrafluoroethylene (PTFE)-based porous sheet (NTF1131; manufactured by Nitto Denko Corporation) was used as a spacer. The thickness of the porous sheet was 75 μm.

The air permeability of the spacer was measured by the above-described method. The air permeability of the spacer was 1.5 sec/100 cm$^3$.

Example 6

A gas detection element was manufactured by a method similar to that of Example 1.

However, in Example 6, kraft paper (double-side PE laminated kraft paper; manufactured by KOMATSU Co., Ltd.) having a thickness of approximately 120 μm was used as a spacer.

Accordingly, a patch-type gas detection element (hereinafter referred to as a "sample 6") was obtained.

Example 7

A patch-type gas detection element (hereinafter referred to as a "sample 7") was manufactured by a method similar to that of Example 1.

However, in Example 7, cardboard (white) having a thickness of 680 μm was used as a spacer.

The air permeability of the spacer was measured by the above-described method. The air permeability of the spacer was 220 sec/100 cm$^3$.

Example 8

A gas detection element was manufactured by a method similar to that of Example 1.

However, in Example 8, no spacer was used. Namely, a gas detection element (hereinafter referred to as a "sample 8") having the backing, the undercoat layer, and the gas detection layer was manufactured.

The following Table 1 outlines the specifications of the spacers included in the samples manufactured in the above Examples.

TABLE 1

| SAMPLE | SPACER MATERIAL | THICKNESS (μm) |
|---|---|---|
| 1 | NON-WOVEN FABRIC | 164 |
| 2 | NON-WOVEN FABRIC | 328 |
| 3 | THERMAL DIFFUSION SHEET | 150 |
| 4 | POROUS SHEET | 70 |
| 5 | POROUS SHEET | 75 |
| 6 | KRAFT PAPER | 116 |
| 7 | CARDBOARD | 680 |
| 8 | NONE | — |

(Evaluation)

The following test was performed by using each of the samples 1 to 8 manufactured by the above-described methods.

A syringe having an inner diameter of 10 mm (capacity 24 ml) was prepared. Open/close valves are provided at both ends (an inlet end and an outlet end) of the syringe, and one opening (through-hole) having a diameter of 2 mm is formed at approximately the middle of the side surface of the syringe.

Next, a sample was attached to the side surface of the syringe, so as to block the through-hole of the syringe. At this time, the sample was attached such that the opening of the through-hole of the syringe is positioned at approximately the center of a spacer of the sample. Note that the sample 8 was attached such that the opening of the through-hole of the syringe is positioned at approximately the center of the gas detection layer.

Next, a hydrogen gas source was coupled to the inlet end of the syringe. Further, the open/close valves of the inlet end and the outlet end were open, and hydrogen gas was passed through the syringe from the inlet end at room temperature. The flow rate of the hydrogen gas was 6 ml/minute, and the flow time was 3 minutes.

After 3 minutes passed, the flow of the hydrogen gas was stopped, and both open/close valves were closed. The sample was observed from the backing side.

The above-described test was performed on each of the samples 1 to 8. Further, the area $S_c$ (hereinafter referred to as a "color change area") of a color change region of each of the samples was measured from the backing side. Then, the ratio $S_c/S_r$ of the color change area to the area $S_r$ of the opening of the through-hole, and the ratio $S_c/S_s$ of the color change area $S_c$ to the area $S_s$ of the spacer were measured.

The following Table 2 outlines test results obtained from the samples 1 to 8.

TABLE 2

| SAMPLE | Ratio $S_c/S_r$ (%) | Ratio $S_c/S_s$ (%) |
|---|---|---|
| 1 | 428 | 121 |
| 2 | 428 | 121 |
| 3 | 796 | 225 |
| 4 | 598 | 169 |
| 5 | 598 | 169 |
| 6 | 510 | 144 |
| 7 | 694 | 196 |
| 8 | 178 | — |

As can be seen from the Table 2, in the sample 8 without a spacer, the ratio $S_c/S_r$ is 178%. Therefore, in the sample 8, hydrogen gas leaking from the opening of the through-hole is less diffused into the gas detection layer of the sample 8.

Conversely, in each of the samples 1 to 7 having the spacers, it can be seen that the ratio $S_c/S_r$ is significantly increased, and further, the ratio $S_c/S_s$ indicates significantly large values.

For the ratio $S_c/S_r$, even the smallest ratio is 428% (the samples 1 and 2). Thus, it can be seen that a color change region in each of the samples 1 and 2 is 4 times or more larger than the area of the opening of the through-hole. For the ratio $S_c/S_s$, even the smallest ratio is 121% (the samples 1 and 2). Thus, it can be seen that hydrogen gas spreads to the outside of the spacer in each of the samples 1 and 2.

In each of the samples 1 to 7, the color change $\Delta L^*$ in a color change region was evaluated by the above-described method. As a result, the color change $\Delta L^*$ was larger than or equal to 10 in each of the samples.

Accordingly, it was verified that a color change region became wider and the visibility of a color change improved by providing the spacer between the gas detection layer and the inspection member.

The present application is based on and claims priority to Japanese patent application No. 2017-153596 filed on Aug. 8, 2017 and Japanese patent application No. 2018-145006, filed on Aug. 1, 2018, with the Japanese Patent Office, the entire contents of which are hereby incorporated by reference.

DESCRIPTION OF THE REFERENCE NUMERAL 1 conventional hydrogen detection tape
10 backing
20 hydrogen gas detection layer
21 color change region
29 adhesive layer
100 first gas detection element
100A strip-shaped First gas detection element
102 first side
104 second side
110, 110A backing
120, 120A gas detection layers
121 color change region
122, 122A first surfaces
124, 124A second surfaces
130, 130A resin matrixes
135, 135A chemochromic pigments
140, 140-1, 140-2, 140-3, 140-4, 140-5, 140-6, 140A spacers
142 contact portion
143A, 143B central rectangular portions
144A, 144B extending portions
146C corner
146D lower side
146S corner
146U upper side
149 gap
150, 150A release liners
154 protruding portion
160A tab portion
180 inspection member
181 first surface
183 second surface
185 hole
187 opening
190 laminate
200 second gas detection element
202 first side
204 second side
210 backing
220 gas detection layer
221 color change region
222 first surface
224 second surface
230 resin matrix
235 chemochromic pigment
243 surface processing portion
245 recessed portion
247 wall portion
248A grooves
248B recess
250 release liner
340 multilayer spacer
342 first side
344 second side
352 body layer
354 first surface
356 second surface
362 adhesive layer
364 first layer
366 second layer
368 third layer
370 non-adhesive region

The invention claimed is:

1. A gas detection element for detection of a measurement target gas, the gas detection element comprising:
    a gas detection layer including a chemochromic pigment, the gas detection layer having a first surface and also having adhesiveness; and
    a spacer, wherein
        the spacer is porous such that it is permeable to the measurement target gas and air, is disposed on the first surface of the gas detection layer, and
        has an area in a plane parallel to the first surface of the gas detection layer that is smaller than an area of the first surface of the gas detection layer, and
    a gap between the spacer and the gas detection layer is formed around a periphery of the spacer, the gap being an empty space fillable by the measurement target gas.

2. The gas detection element according to claim 1, wherein the spacer is selected from a group consisting of:
    paper made of pulp;
    a non-woven fabric or a woven fabric, including fibers of an inorganic material selected from the group consisting of glass, ceramic, and metal, or including fibers of a polymer material;
    a thermal diffusion sheet including an inorganic material selected from the group consisting of glass, ceramic, and metal, or including a polymer material;
    a porous sheet including an inorganic material selected from the group consisting of glass, ceramic, and metal, or including a polymer material; and
    a foam having connected pores.

3. The gas detection element according to claim 1, wherein at least a part of an end surface of the spacer is exposed to outside.

4. The gas detection element according to claim 1, wherein a periphery of the spacer is surrounded by the gas detection layer in top view.

5. The gas detection element according to claim 1, wherein the spacer has a thickness in a range from 5 μm to 1000 μm.

6. The gas detection element according to claim 1, wherein a ratio Ss/Sg is in a range from 0.02 to 0.9, in which Ss represents an area of the spacer and Sg represents an area of the gas detection layer in top view.

7. The gas detection element according to claim 1, further comprising a release liner on the first surface of the gas detection layer.

8. The gas detection element according to claim 1, further comprising a backing on a second surface of the gas detection layer opposite to the first surface.

9. The gas detection element according to claim 8, wherein the backing is formed of polyimide, polyethylene (PE), polypropylene (PP), a fluorinated ethylene propylene copolymer (FEP), an ethylene tetrafluoroethylene copolymer (ETFE), polytetrafluoroethylene (PTFE), polyethylene terephthalate (PET), a tetrafluoroethylene-perfluoroalkyl vinyl ether copolymer (PFA), or polyvinylidene fluoride (PVDF).

10. The gas detection element according to claim 1, wherein the chemochromic pigment changes in color by contacting a reducing gas.

11. The gas detection element according to claim 1, wherein the chemochromic pigment includes palladium oxide on surfaces of carrier particles, a noble metal other than palladium being carried by or doped into the palladium oxide.

12. The gas detection element according to claim 11, wherein the carrier particles include titanium oxide.

13. The gas detection element according to claim 1, wherein the gas detection layer includes a silicone resin.

14. The gas detection element according to claim 13, wherein the silicone resin includes a phenylmethyl group or a dimethyl group.

15. The gas detection element according to claim 1, wherein the gas detection element is in a form of a patch or in a form of a strip.

16. The gas detection element according to claim 1, wherein the measurement target gas is hydrogen gas.

17. The gas detection element according to claim 1, wherein the area of the spacer is substantially larger than an opening in an inspection member, and the measurement target gas is introduced through the opening.

* * * * *